United States Patent
Huang et al.

(10) Patent No.: US 12,053,472 B2
(45) Date of Patent: Aug. 6, 2024

(54) PHARMACEUTICAL COMPOSITION FOR TREATING LOCALLY ADVANCED MISMATCH REPAIR-PROFICIENT/MICROSATELLITE STABLE (PMMR/MSS) COLORECTAL CANCER (CRC) AND USE THEREOF

(71) Applicant: The Sixth Affiliated Hospital, Sun Yat-sen University, Guangdong (CN)

(72) Inventors: Jun Huang, Guangdong (CN); Meijin Huang, Guangdong (CN); Yanhong Deng, Guangdong (CN); Fengyun Pei, Guangdong (CN); Jianping Wang, Guangdong (CN)

(73) Assignee: The Sixth Affiliated Hospital, Sun Yat-sen University, Guangzhou (CN)

( * ) Notice: Subject to any disclaimer, the term of this patent is extended or adjusted under 35 U.S.C. 154(b) by 0 days.

(21) Appl. No.: 18/099,291

(22) Filed: Jan. 20, 2023

(65) Prior Publication Data
US 2023/0285395 A1   Sep. 14, 2023

(30) Foreign Application Priority Data
Jan. 24, 2022 (CN) .......................... 202210083399.9

(51) Int. Cl.
*A61K 31/513* (2006.01)
*A61K 31/4188* (2006.01)
(Continued)

(52) U.S. Cl.
CPC ........ *A61K 31/513* (2013.01); *A61K 31/4188* (2013.01); *A61K 31/555* (2013.01); *A61P 35/00* (2018.01)

(58) Field of Classification Search
CPC .............. A61K 31/513; A61K 31/4188; A61K 31/555; A61K 31/337; A61K 31/519;
(Continued)

(56) References Cited

FOREIGN PATENT DOCUMENTS

WO    WO-2020225552 A1 *  11/2020    ........... A61K 31/282

OTHER PUBLICATIONS

American Cancer Society. Understanding Advanced and Metastatic Cancer. cancer.org/cancer/managing-cancer/advanced-cancer/what-is.html. Last revised Sep. 10, 2020 (Year: 2020).*

(Continued)

*Primary Examiner* — Valerie Rodriguez-Garcia
*Assistant Examiner* — Kyle Nottingham

(57) ABSTRACT

Disclosed are a pharmaceutical composition for treating locally advanced mismatch repair-proficient/microsatellite stable (pMMR/MSS) colorectal cancer (CRC) and use thereof. The pharmaceutical composition of the present disclosure includes mFOLFOX6, bevacizumab, and a PD-1 inhibitor. Experimental results show that, when the pharmaceutical composition is used to treat 18 locally advanced (T4NxMO) MSS CRC cases, major pathological remission (tumor regression exceeds 90%) is achieved in 14 cases and pathological complete remission (no residual tumor cells) is achieved in 10 cases; tumor marker levels are all lowered to normal levels; there is no fatal serious adverse event (SAE); and the pharmaceutical composition has prominent safety and efficacy. For locally advanced (T4NxMO) pMMR/MSS CRC patients, the pharmaceutical composition can be administered in combination to make a tumor regress, to improve an R0 resection rate and a pathological complete response (pCR) rate and avoid toxic and side effects of three-drug chemotherapy and concurrent chemoradiotherapy.

3 Claims, 1 Drawing Sheet

(51) Int. Cl.
*A61K 31/555* (2006.01)
*A61P 35/00* (2006.01)

(58) Field of Classification Search
CPC .............. A61K 31/704; A61K 31/7068; A61K 9/0019; A61K 39/3955; A61K 2039/507; A61P 35/00
See application file for complete search history.

(56) References Cited

OTHER PUBLICATIONS

American Cancer Society. Colorectal Cancer Stages. cancer.org/cancer/types/colon-rectal-cancer/detection-diagnosis-staging/staged.html. Last revised Jun. 29, 2020 (Year: 2020).*

Fang, Chongkai et al. "Metastatic Colorectal Cancer Patient with Microsatellite Stability and BRAFV600E Mutation Showed a Complete Metabolic Response to PD-1 Blockade and Bevacizumab: A Case Report." Frontiers in Oncology, vol. 11, 2021 (Year: 2021)—Supplementary Fig. 2.*

Vukobrat-Bijedic, Zora, et al. "Cancer Antigens (CEA and CA 19-9) as Markers of Advanced Stage of Colorectal Carcinoma." Medical Archives (Sarajevo, Bosnia and Herzegovina), vol. 67, No. 6, Dec. 2013, pp. 397-401. (Year: 2013).*

Chongkai Fang et al., Metastatic Colorectal Cancer Patient With Microsatellite Stability and BRAFV600E Mutation Showed a Complete Metabolic Response to PD-1 Blockade and Bevacizumab: A Case Report, Frontiers in Oncology, Apr. 27, 2021, pp. 1-6, vol. 11.

Chinese College of Surgeons et al., China guideline for diagnosis and comprehensive treatment of colorectal liver metastases (2020 edition), J Clin Hepatol, Mar. 2021, pp. 543-553, vol. 37, No. 3.

Meng Qiu et al., Comparison of Efficacy and Safety of Pembrolizumab Versus Standard Therapy in the First-Line Treatment of Patients With MSI-H/dMMR Metastatic Colorectal Cancer, The Journal of Evidence-Based Medicine, Aug. 2020, pp. 227-231, vol. 20, No. 4.

J. B. A. G. Haanen et al., Management of toxicities from immunotherapy: ESMO Clinical Practice Guideline for diagnosis, treatment and follow-up, Annals of Oncology, Aug. 2017, pp. i119-i142, vol. 28, Supplement 4.

* cited by examiner

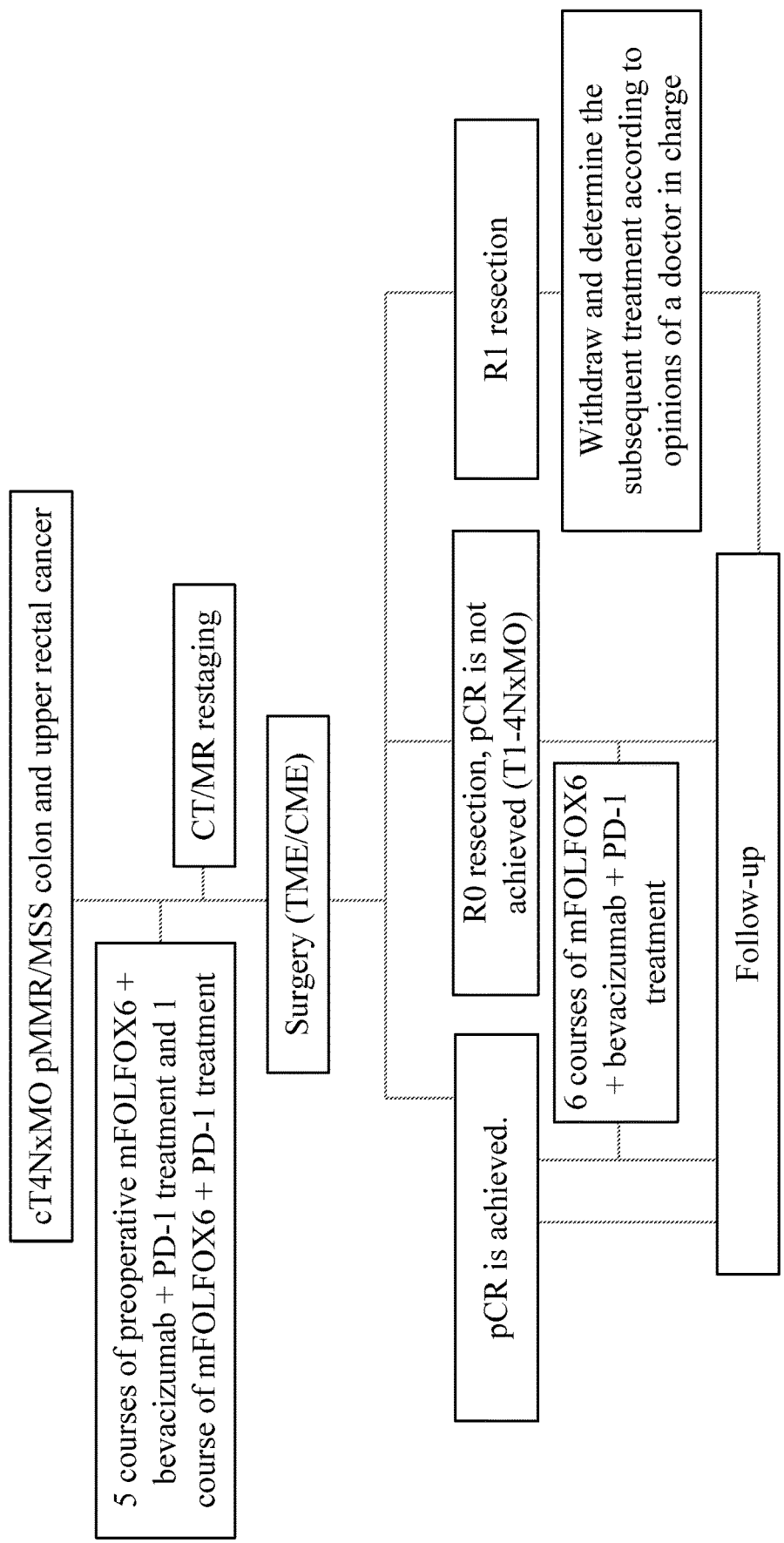

PHARMACEUTICAL COMPOSITION FOR TREATING LOCALLY ADVANCED MISMATCH REPAIR-PROFICIENT/MICROSATELLITE STABLE (PMMR/MSS) COLORECTAL CANCER (CRC) AND USE THEREOF

CROSS-REFERENCE TO RELATED APPLICATION

The present application claims priority from Chinese Patent Application No. 202210083399.9 filed on Jan. 24, 2022, the contents of which are incorporated herein by reference in their entirety.

TECHNICAL FIELD

The present disclosure relates to the technical field of medicine, and in particular to a pharmaceutical composition treating locally advanced (T4N×M0) mismatch repair-proficient/microsatellite stable (pMMR/MSS) colorectal cancer (CRC) and use thereof.

BACKGROUND

CRC is one of the most common malignant tumors in humans. At present, radical resection-preoperative neoadjuvant chemotherapy is still the standard comprehensive treatment mode recommended by the NCCN and ESMO international guidelines and the Chinese CSCO guidelines for treating CRC. The mismatch repair (MMR) protein expression and the microsatellite stable (MSS) status are important factors affecting the efficacy of immunotherapy. In the past two or three years, the PD-1 monoclonal antibody (mAb) immunotherapy exhibits a significant therapeutic effect in the second-line/first-line treatment of advanced DNA mismatch repair-deficient/microsatellite instability-high (dMMR/MSI-H) CRC and the neoadjuvant therapy of early-stage colon cancer, with high therapeutic safety and controllable toxicity. However, the above cases account for only 8% to 10% of all CRC cases, and 90% of CRC patients are pMMR/MSS.

Locally advanced CRC (T4N×M0) is often difficult to undergo one-stage R0 resection because a local tumor penetrates a serosal layer and an abdominal wall or infiltrates and invades surrounding organs, and the failure of R0 resection means that the tumor is still there and can no longer be cured and the patient has no choice but to wait for death. For MSS (MSI-H) CRC, the administration of PD-1 alone or in combination with other immunotherapy has become the first-line treatment of choice. mFOLFOXIRI is currently one of the common regimens for neoadjuvant or conversion downstaging of locally advanced CRC, which has a tumor downstaging rate of about 41% in locally advanced rectal cancer, but leads to larger side effects than mFOLFOX6. In addition, capecitabine-containing chemotherapeutic drugs (CapeOX) can be used. The combination of capecitabine and oxaliplatin for first-line treatment is similar to the FOLFOX6 combination in response rate, disease progression time, and overall survival (OS) period. In addition to conventional chemotherapy, neoadjuvant chemotherapy is often used clinically, which refers to systemic chemotherapy of a patient before surgery. Neoadjuvant chemotherapy is suitable for a tumor that is difficult to be resected by surgery and can hardly be completely removed. Currently, there is no clear standard regimen for treating locally advanced (T4N×M0) MSS CRC.

SUMMARY

The present disclosure is intended to overcome the above-mentioned deficiencies in the prior art and provide a pharmaceutical composition for treating locally advanced (T4N×M0) pMMR/MSS CRC and use thereof.

To achieve the above objective, the present disclosure adopts the following technical solutions:

A first objective of the present disclosure is to provide a pharmaceutical composition for treating locally advanced (T4N×M0) pMMR/MSS CRC, including mFOLFOX6, bevacizumab, and a PD-1 inhibitor.

As a preferred embodiment of the pharmaceutical composition of the present disclosure, mFOLFOX6 may include oxaliplatin and fluorouracil/capecitabine. The PD-1 inhibitor may include an anti-PD-1 antibody and an anti-PD-L1 antibody.

As a preferred embodiment of the pharmaceutical composition of the present disclosure, the pharmaceutical composition may further include a pharmaceutically acceptable carrier.

As a preferred embodiment of the pharmaceutical composition of the present disclosure, the pharmaceutical composition may be in an injection dosage form. More preferably, the pharmaceutical composition may include mFOLFOX6, a bevacizumab injection, and a recombinant humanized anti-PD-1 mAb injection.

A second objective of the present disclosure is to provide use of the pharmaceutical composition described above in the preparation of a drug for treating locally advanced (T4N×M0) pMMR/MSS CRC.

As a preferred embodiment of the use of the present disclosure, the pharmaceutical composition described above may be administered for 5 courses of treatment before surgery, and if pathological complete remission is not achieved three to four weeks after surgery, the pharmaceutical composition described above may be further administered for 6 courses of treatment.

As a preferred embodiment of the use of the present disclosure, the pharmaceutical composition can increase a pathological complete response (pCR) rate and a major pathological response (mPR) rate.

As a preferred embodiment of the use of the present disclosure, imaging and biological efficacy evaluation may be conducted after the pharmaceutical composition described above is initially administered for 3 courses of treatment, and if an imaging result shows tumor regression and a decline in a detection value of a tumor marker, the follow-up neoadjuvant or conversion therapy may be further conducted.

As a preferred embodiment of the use of the present disclosure, the biological efficacy evaluation may include pelvic magnetic resonance (MR) scan+enhancement, chest and upper and lower abdominal computerized tomography (CT) scan+enhancement, and detection of tumor markers carcinoembryonic antigen (CEA) and cancer antigen 19-9 (CA19-9).

The pharmaceutical composition of the present disclosure includes mFOLFOX6, bevacizumab, and a PD-1 inhibitor. Prior art has not disclosed using this particular pharmaceutical combination to treat locally advanced (T4N×M0) pMMR/MSS CRC. Experimental results show that, when the pharmaceutical composition is used to treat 18 locally advanced MSS CRC cases, major pathological remission (tumor regression exceeding 90%) is achieved in 14 cases and pathological complete remission (no residual tumor cells) is achieved in 10 cases; tumor markers all return to normal levels; there is no fatal serious adverse event (SAE). These results show that the pharmaceutical composition has good safety records and high efficacy. Conclusively, for locally advanced (T4N×M0) pMMR/MSS CRC patients, the pharmaceutical composition of the present disclosure can be administered in combination to induce greatest tumor regression and thus greatest R0 resection rate and pCR rate, while preventing the toxic and side effects brought by three-drug chemotherapy and concurrent chemoradiotherapy.

In the present disclosure, an open-label, multi-center phase II study is conducted to assess the safety and efficacy of the pharmaceutical composition in a combination treatment of a locally advanced MSS CRC patient. This study provides definite clinical evidence for personalized precision treatment of CRC patients and demonstrates that the functions and organs of locally advanced pMMR/MSS CRC patients can be protected to the greatest extent, and quality of life of these patients can be significantly improved.

Compared with the prior art, the present disclosure has the following beneficial effects: The present disclosure provides a pharmaceutical composition including mFOLFOX6, bevacizumab, and a PD-1 inhibitor. The pharmaceutical composition can be used for treating locally advanced (T4N×M0) pMMR/MSS CRC with increased pCR rate and mPR rate. The treatment is safe and effective.

BRIEF DESCRIPTION OF THE DRAWINGS

The sole FIGURE is a flow chart of an experiment of the present disclosure.

DETAILED DESCRIPTION

To better explain the objectives, technical solutions, and advantages of the present disclosure, the present disclosure will be further explained below with reference to the accompanying drawing and specific examples.

In the following examples, unless otherwise specified, the experimental methods used are conventional, and the materials and reagents used are commercially available.

Example 1

Inclusion Criteria:
1) Histological identified colon and upper rectum adenocarcinoma;
2) Tumor biopsy immunohistochemical (IHC) identified pMMR, including all of the MSH1, MSH2, MSH6 and PMS2 protein expression and diagnosed as proficient mismatch repair (pMMR), or next generation sequencing identified (MSS); MRI identified tumor inferior margin higher than peritoneal reflection;
3) Clinical staging T4N×M0, with or without positive MRF, with or without positive EMVI;
4) Staging method: all patients undergo chest, abdominal and pelvic enhanced CT, rectal palpation, high resolution MRI examination, positive perienteric lymph node (LN): short diameter ≥10 mm LN or LN with typical metastatic shape and MRI character, clinical data should be re-evaluated and judged by center evaluation group when there are contradictory stagings, distant metastasis were excluded by chest and abdominal enhanced CT and pelvic enhanced MRI;
5) No intestinal obstruction symptom, or obstruction relieved after proximal colostomy;
6) No rectal surgery history; No chemotherapy or radiotherapy history; No biopharmaceutical treatment history (such as monoclonal antibody), immunotherapy (such as anti PD-1 antibody, anti PD-L1 antibody, anti PD-L2 antibody or anti CTLA-4), or other research drug treatment; Endocrinotherapy history restriction: No; informed consent assigned;
7) Subject characteristics: 18 to 80 years old; performance Status Scale: ECOG 0-1; life expectancy: more than 2 years; hematology: WBC>$3\times10^9$/L, PLT>$80\times10^9$/L, and Hb>90 g/L; liver function: alanine transaminase (ALT) and aspartate aminotransferase (AST) levels: 2 times lower than normal levels; bilirubin: 1.5 times lower than the normal level; renal function: creatinine level: 1.5 times lower than the normal level or creatinine clearance rate (CCr): higher than or equal to 60 mL/min.

Exclusion Criteria:
1) Arrhythmia need anti-arrhythmia treatment (except ß-blocking agent or Digoxin), symptomatic coronary heart disease or myocardial ischemia (myocardial infarction within 6 months) or congestive heart-failure (CHF)>NYHA grade II;
2) Severe hypertension not well controlled by drugs;
3) HIV infection history or active phase of chronic Hepatitis B or C (high copies of virus DNA);
4) Active tuberculosis (TB), accepting anti-TB treatment or anti-TB treatment within 1 year before trial screen;
5) Other active clinical severe infection (NCI-CTC V5.0),
6) Outside pelvic distant metastasis evidences,
7) Dyscrasia, organ dysfunction,
8) Pelvic or abdominal radiotherapy history,
9) Multiple CRC or Multi-primary tumors;
10) Epilepsy need treatments (Steroid or anti-epilepsy therapy),
11) Other malignant tumor history within 5 years,
12) Over abuse of drugs, medical and psychological or social conditions that might interfere patients or evaluation of the study results,
13) Any active autoimmune disease or autoimmune disease history (including but not restricted: interstitial pneumonia, uveitis, enteritis, hepatitis, hypophysitis, nephritis, hyperthyroidism, hypothyroidism, asthma need bronchodilators),
14) Any anti-infection vaccine injection 4 weeks before inclusion,
15) Long-term exposure to immune-suppressor, combination of systemic or topical use of corticosteroids (dose>10 mg/day prednisolone or equivalent hormone);
16) Known or suspicious allergy to any study related drugs; Any unstable state might cause damage to the safety and compliance of patients; Pregnant or breast feeding women who has ability to have children while without contraception; Refuse to sign informed consent 3. Validation of Sample Size:

Simon's optimal two-stage design was adopted in this study.

The enrolled patients were MSS colon and upper rectal cancer patients. With reference to the pCR rate of 4% for FOXTROT and single-standard OPTICAL in the treatment of locally advanced rectal cancer, a maximum invalid cut-off value was set to 0.2, a minimum effective cut-off value was set to 0.04, $\alpha=0.05$, $\beta=0.1$. Sample size at the first stage was 19. At least one person must reach pCR, otherwise the study would fail; and if one person reaches pCR, subject recruitment for the second stage could begin. 19 subjects were recruited for the second stage. Given the case loss of 10%, a required sample size was calculated to be 42.

4. Composition of a Pharmaceutical Composition:

A pharmaceutical composition for treating locally advanced (T4NxM0) pMMR/MSS CRC in the present disclosure was composed of mFOLFOX6 (oxaliplatin+fluorouracil/capecitabine), a bevacizumab injection, and a recombinant humanized anti-PD-1 mAb injection.

The bevacizumab injection and recombinant humanized anti-PD-1 mAb injection were obtained from Innovent Biologics (Suzhou) Co. Ltd.

The recombinant humanized anti-PD-1 mAb injection included the following components: recombinant fully human anti-programmed death receptor 1 mAb (100 mg), 140 mmol/L mannitol, 25 mmol/L histidine, 20 mmol/L sodium citrate dihydrate, 50 mmol/L sodium chloride, 0.02 mmol/L disodium edetate (ethylenediaminetetraacetic acid (EDTA) disodium), 0.2 mg/ml polysorbate 80, and had a pH of 6.0.

The bevacizumab injection included the following components: bevacizumab, sodium acetate, sorbitol, polysorbate 80, glacial acetic acid, and water for injection (WFI), and had a pH of 6.0.

5. Experimental Method:

1) pMMR/MSS colon and upper rectal cancer patients signed an informed consent form (from December 2020 to June 2021, the study recruited 18 patients with clinical stage T4NxM0 (AJCC 8th edition) locally advanced colon cancer or upper rectal cancer. These patients were admitted to The Sixth Affiliated Hospital of Sun Yat-Sen University).

2) After 3 courses of mFOLFOX6+bevacizumab+PD-1 inhibitor treatment were initially completed (to ensure that the radical surgery could conduct as scheduled, the last neoadjuvant therapy was conducted without the bevacizumab injection), imaging and biological efficacy evaluation was conducted, and if the imaging result showed tumor regression and a decline in a detection value of a tumor marker, follow-up neoadjuvant or conversion therapy was further conducted.

3) All patients were injected with 200 mg of the recombinant humanized anti-PD-1 mAb through intravenous drip for 30 min to 60 min on day 1 of each course over 2 weeks, Q2W. After completing 6 courses of preoperative treatment, CT/MR was conducted for restaging and surgeries were scheduled. Approximately 12 weeks after the initial neoadjuvant therapy, radical resection was scheduled to take place.

4) pCR patients confirmed by postoperative pathology could further undergo 6 courses of mFOLFOX6+bevacizumab+PD-1 inhibitor (i.e., the aforementioned pharmaceutical composition) treatment three to four weeks after surgery; or the patient was reexamined every three months in the first year, every six months in the second and third years, and annually in the fourth and fifth years after surgery. Patients who did not reach pCR after R0 resection were further subjected to 6 courses of mFOLFOX6+bevacizumab+PD-1 inhibitor (i.e., the aforementioned pharmaceutical composition) three to four weeks after surgery, and if there was still residual tumor after 6 courses of preoperative treatment or RI resection, it was necessary to withdraw and change the treatment regimen according to opinions of a doctor in charge.

5) Each efficacy evaluation included pelvic MR (scan+enhancement), chest and upper and lower abdominal CT (scan+enhancement), and detection of tumor markers CEA and CA19-9. The pCR rate in the cohort of patients was adopted as a primary endpoint of the present disclosure. The present disclosure also evaluated mPR rates, radiological and pathological regressions, safety, tumor mutational burden (TMB), and tumor microenvironment (TME) molecules. An flow chart of the experiment could be seen in the sole FIGURE.

It should be noted that the PD-1 inhibitor (sintilimab) of the present disclosure cannot be injected by IV bolus injection or rapid injection. Peripheral or central venous access should be established. Before infusion, sufficient epinephrine, intravenous diphenhydramine hydrochloride, or other anti-allergic drugs and resuscitation equipment should be prepared so that they are readily available in the event of a severe allergic reaction. After infusion, venous access should remain open to facilitate further administration as needed. If there are no complications, the patient should be put under observation for 1 h before withdrawing intravenous access. Toxicity management was conducted according to "*Management of Toxicities from Immunotherapy: ESMO Clinical Practice Guideline for diagnosis, treatment and follow-up*", 2018.

Before treatment, the patients were subjected to anti-allergic pretreatment, intensive ECG monitoring, and close monitoring of vital signs. If serious adverse reactions occur, the treatment will be discontinued as soon as possible and active treatment measures such as cardiopulmonary, liver, and kidney function protection support and anti-inflammatory storm therapy will be conducted. The dose of the PD-1 inhibitor in the present disclosure does not need to be adjusted. The investigated treatment of the subject may be paused in the event of an adverse event necessitating the suspension of administration; the administration of sintilimab may then be delayed for up to 7 days as a result of the adverse event, and the administration schedule may be postponed accordingly. Delayed dosing for more than 7 days is considered a missed dose, and the subject receives the next dose according to the original dosing schedule (from the date of the first dosing). Permanent withdrawal from study is considered if the subject is discontinued for more than 56 days and the investigator judges that the risks of continuing sintilimab treatment outweigh the benefits.

Surgical Specifications:

CRC Surgery: Laparotomy or Laparoscopy.

With laparoscopy as an example: endotracheal intubation under general anesthesia. The median incision is adopted for the former, and the 4-5 trocar technique is usually adopted for the latter: pneumoperitoneum is established and a laparoscopic instrument is inserted.

The operation is roughly divided into the following steps: 1) After abdominal exploration, an admission passage from inside to outside is taken and inferior mesenteric blood vessels are ligated and cut off, with the left ureter, reproductive blood vessels, and superior hypogastric nerves protected. The descending colons are fully dissociated, and the splenic flexure is dissociated if necessary. 2) According to the CME/TME principle, the colon and total mesorectum are subjected to sharp excision, with the surrounding organs such as prostate, vagina, and pelvic nerves protected. 3) For those who can undergo ultra-low anterior resection (LAR) by double-stapling technique, internal sphincterotomy is not necessary (excluding cases); and for those who must undergo internal sphincterotomy, transanal procedures should be adopted (the same as above).

The surgery described above should be conducted by a gastrointestinal surgeon at deputy senior level or above and with 5 or more years of clinical experience in laparoscopic radical resection of CRC as the chief surgeon. Before the project enters the implementation stage, doctors need to undergo unified training.

Discharge criteria after surgery: Good general conditions, diet and bowel functions basically returned to normal; normal body temperature, and no positive signs observed during abdominal examination; relevant laboratory test results basically normal; and the perineal incision and/or abdominal incision heal well (II/A or II/B).

6. Evaluation of Experimental Results:
1) Pathological Complete Remission Evaluation:

There were no residual tumor cells in the primary lesions and regional lymph nodes of a surgical specimen. A third-party unit or individual (pathological and imaging evaluation) independent of the study was invited for an independent blind evaluation, and the evaluation result was subjected to consistency evaluation with the evaluation result from the research group. The research results were reported mainly based on an analysis and determination from the research group, and was supplemented by the analysis and evaluation of the third-party.

2) Evaluation of Local Recurrence or Metastasis:

When clinical symptoms (such as anal pain, bloody stool, and lower limb edema) occur, CEA level progressively increases, or suspicious signs are observed in chest or abdominal images, further examination is required to find local recurrence or disease metastasis progression. Local regional recurrence mainly refers to tumor recurrence in a local area of a surgical process or a nearby lymphatic drainage area and adjacent organs. Distant metastasis refers to tumor recurrence outside the above-mentioned areas. Disease-free survival (DFS) means that no tumor recurrence or new CRC is found in a patient by systematic evaluation.

The diagnosis of clinical recurrence and metastasis must meet at least one of the following:
  A. an imaging result suggests recurrence (ultrasound, CT, MRI, and PET-CT) and
  B. Positive cytology biopsy (ascitic fluid appearance, anastomosis recurrence, and suspicious imaging findings).

The reported date of recurrence refers to the date on which the recurrence is discovered by the above diagnosis method. When the recurrence occurs, an investigator should indicate a site of recurrence and a diagnosis method used. When clear imaging evidence is not available, a positive cytology or biopsy result should be acquired. The increased CEA level alone cannot be used as evidence for local recurrence or metastasis of rectal cancer.

3) Calculation of a Survival Period

DFS is defined as a time interval from the enrollment to the occurrence of the event next time. The tumor assessment (CT/MRI of abdomen and pelvis or ultrasound and chest CT) and tumor marker detection must be conducted every 6 or 12 months after enrollment or when a patient undergoes progression signs (namely, clinical indications). Suspicious lesions detected by ultrasonography must be confirmed by CT/MRI. All reoperations or further anticancer treatments should also be recorded.

According to the objective of this study, an event to determine that a patient is no longer in DFS is defined as follows:
  i) a patient has signs of recurrence and metastasis of the original tumor;
  ii) a patient has new signs of CRC; and
  iii) there is death caused by any reason.

Note: The recurrence of the original tumor or the occurrence of new CRC should be confirmed by a cytological or histological method. If there is no supporting evidence from other targeted inspection results (such as radiology and histology/cytology), an isolated event such as CEA increase or unexplained clinical disease progression cannot be used as a basis for determining recurrence. A recurrence date is defined as the final confirmation date of targeted inspection results. Patients will thereafter undergo planned survival follow-up.

If the confirmed recurrence of CRC or the development of new CRC occurs at the investigated treatment stage, a corresponding patient will withdraw from the investigated treatment and will be subjected to survival follow-up. If the recurrence of CRC or the development of new CRC occurs at the investigated treatment stage, a corresponding patient can be further treated according to the guidance of an investigator.

An OS period is defined as a time interval from enrollment to a date of death or last follow-up. All test patients will be subjected to follow-up for at least 5 years. If a biopsy is conducted, a biopsy report should be provided. The OS period refers to a time interval from enrollment to death. Regardless of the death cause, for patients whose death information is not collected in the clinical database, the most recent known survival date is determined as a cut-off point. If a patient survives all the time, a time interval from the cut-off point to the last follow-up is determined as the OS period.

4) Evaluation of Toxic and Side Effects of Neoadjuvant Therapy/Adjuvant Therapy

The toxicity evaluation is conducted according to the CTCAE standard (version 5.0), and the follow-up to evaluate patient safety should be conducted during the treatment period and a period of 30 days after the last cycle.

7. Experimental Results:

As of data cutoff (Dec. 31, 2021), median follow-up was 4.5 months (IQR 1.5-9.4). All patients underwent R0 surgical resection without treatment-related surgical delays. Of the 18 tumors that were removed, 18 were completely resected. A pCR occurred in 10 of 18 resected tumors (56%) and a major pathological response (MPR, ≤10% residual viable tumor) in 14/18 (78%).

At data cutoff, 18 were alive and 17 were free of recurrence. Treatment-related adverse events of grade 3 or higher occurred in 10% of the patients. Among the pCR tumors, two were found to harbored POLE mutation. The degree of pathological regression was deeper than radiological tumor shrinkage. The expression of CD3+ or/and CD3+/CD4+ stroma around tumor in pretreated tissue was significantly lower when comparing pCR and non-pCR (both p=0.024).

The above experiments show that the neoadjuvant treatment regimen with the combined administration of mFOLFOX6 (oxaliplatin+fluorouracil/capecitabine), a bevacizumab injection, and a recombinant humanized anti-PD-1 mAb injection has prominent safety and efficacy, and can achieve a pCR rate of 56% and an mPR rate of 78% with few neoadjuvant therapy-associated adverse events. The stromal downregulation of CD3 or CD3/CD4 expression correlates with pCR (NCT).

Finally, it should be noted that the above embodiments are provided merely to describe the technical solutions of the present disclosure, rather than to limit the protection scope of the present disclosure. Although the present disclosure is described in detail with reference to preferred embodiments, a person of ordinary skill in the art should understand that modifications or equivalent replacements may be made to the technical solutions of the present disclosure without departing from the spirit and scope of the technical solutions of the present disclosure.

The invention claimed is:

1. A method for treating locally advanced microsatellite stable (MSS) colorectal cancer (CRC), comprising administering a pharmaceutical composition for 5 courses of treatment prior to a surgery; and administering the pharmaceutical composition for another 6 courses of treatment if pathological complete remission is not achieved three to four weeks after the surgery;

wherein the pharmaceutical composition comprises mFOLFOX6, bevacizumab, and a PD-1 inhibitor;

wherein the method further comprises conducting imaging and biological efficacy evaluation after the pharmaceutical composition is administered for 3 courses of treatment; and conducting follow-up neoadjuvant or translational therapy if an imaging result shows tumor regression and a decline in a detection value of a tumor marker.

2. The method according to claim 1, wherein the pharmaceutical composition is able to increase a pathological complete response (pCR) rate and a major pathological response (mPR) rate.

3. The method according to claim 1, wherein the imaging and biological efficacy evaluation comprises pelvic magnetic resonance (MR) scan+enhancement, chest and upper and lower abdominal computerized tomography (CT) scan+enhancement, and detection of tumor markers carcinoembryonic antigen (CEA) and cancer antigen 19-9 (CA19-9).

* * * * *